United States Patent
Rubinfeld

(10) Patent No.: US 6,420,378 B1
(45) Date of Patent: Jul. 16, 2002

(54) INHIBITION OF ABNORMAL CELL PROLIFERATION WITH CAMPTOTHECIN AND COMBINATIONS INCLUDING THE SAME

(75) Inventor: Joseph Rubinfeld, Danville, CA (US)

(73) Assignee: SuperGen, Inc., Dublin, CA (US)

( * ) Notice: Subject to any disclaimer, the term of this patent is extended or adjusted under 35 U.S.C. 154(b) by 0 days.

(21) Appl. No.: 09/553,710

(22) Filed: Apr. 20, 2000

Related U.S. Application Data

(63) Continuation-in-part of application No. 09/418,862, filed on Oct. 15, 1999, now Pat. No. 6,191,119.

(51) Int. Cl.[7] ............. A61K 31/44; A61K 39/395; A61K 34/40; A61K 34/42
(52) U.S. Cl. ............................ 514/283; 424/142.1
(58) Field of Search ..................... 514/283; 424/142.1

(56) References Cited

U.S. PATENT DOCUMENTS 5,552,154 A * 9/1996 Giovanella et al. ......... 514/283

OTHER PUBLICATIONS

Baselga et al., Cancer Res. (1998), 58(13), 2825–2831 Abstract Only.*

* cited by examiner

*Primary Examiner*—Jerome D. Goldberg
(74) *Attorney, Agent, or Firm*—David J. Weitz; Wilson Sonsini Goodrich & Rosati

(57) ABSTRACT

A method for treating diseases associated with abnormal cell proliferation comprises delivering to a patient in need of treatment a compound selected from the group consisting of 20(S)-camptothecin, analog of 20(S)-camptothecin, derivative of 20(S)-camptothecin, prodrug of 20(S)-camptothecin, and pharmaceutically active metabolite of 20(S)-camptothecin, in combination with an effective amount of one or more agents selected from the group consisting of alkylating agent, antibiotic agent, an alkylating agent, antibiotic agent, antimetabolic agent, hormonal agent, plant-derived agent, anti-angiogenesis agent and biologic agent. The method can be used to treat benign tumors, malignant or metastatic tumors, leukemia and diseases associated with abnormal angiogenesis.

3 Claims, No Drawings

INHIBITION OF ABNORMAL CELL PROLIFERATION WITH CAMPTOTHECIN AND COMBINATIONS INCLUDING THE SAME

RELATIONSHIP TO COPENDING APPLICATIONS

This application is a CIP of "COMBINATION THERAPY INCLUDING CAMPTOTHECIN", application Ser. No.: 09/418,862; Filed: Oct. 15, 1999 now U.S. Pat. No. 6,191,119B1.

FIELD OF THE INVENTION

This invention relates to a method for treating diseases using a camptothecin, and more specifically a method for treating diseases associated with abnormal cell growth using a camptothecin alone or in combination with another drug.

DESCRIPTION OF RELATED ART

20(S)-camptothecin, a plant alkaloid, was found to have anticancer activity in the late 1950's. Wall, M. et al., *Plant antitumor agents. I. The isolation and structure of camptothecin,. a novel alkaloidal leukemia and tumor inhibitor from Camptotheca acuminata*, J. Am. Chem. Soc. 88: 3888–3890, (1966); Monroe E. Wall et al., *Camptothecin: Discovery to Clinic*, 803 Annals of the New York Academy of Sciences 1 (1996). These documents, and all documents (articles, patents, etc.) cited to herein, are incorporated by reference into the specification as if reproduced fully below. The chemical formula of camptothecin was determined to be $C_{20} H_{16} N_2 O_4$.

20(S)-camptothecin itself is insoluble in water. However, during the sixties and seventies the sodium salt of 20(S)-camptothecin was derived from 20(S)-camptothecin through opening of the lactone ring using a mild base. Clinical trials were then conducted using this hydrosoluble, sodium salt derivative of 20(S)-camptothecin (20(S)-camptothecin Na+), which was administered intravenously. The studies were later abandoned because of the high toxicity and low potency of 20(S)-camptothecin Na+. Gottlieb, J. A., et al., *Preliminary pharmacological and clinical evaluation of camptothecin sodium salt (NSC 100880)*, Cancer Chemother. Rep. 54:461–470 (1979); Muggia, F. M., et al., *Phase I clinical trials of weekly and daily treatment with camptothecin (NSC 100880): Correlation with clinical studies*, Cancer Chemother. Rep. 56:515–521 (1972); Gottlieb, J. A. et al., *Treatment of malignant melanoma with camptothecin (NSC 100880)*, Cancer Chemother. Rep. 56:103–105 (1972); and Moertel, C. G., et al., *Phase II study of camptothecin (NSC 100880) in type treatment of advanced gastrointestinal cancer*, Cancer Chemother Rep. 56:95–101 (1972).

Despite its potential, interest in 20(S)-camptothecin as a therapeutic remained at a low ebb until the mid-1980's. By that time, drug therapies were being evaluated for treating human cancer using human cancer xenograft lines. During these evaluations, human tumors are serially heterotransplanted into immunodeficient, so-called nude mice, and the mice then tested for their responsiveness to a specific drug. (Giovanella, B. C., et al., Cancer 52(7): 1146 (1983)). The data obtained in these studies strongly support the validity of heterotransplanted human tumors into immunodeficient mammals, such as nude mice, as a predictive model for testing the effectiveness of anticancer agents.

20(S)-camptothecin, and later some of its substituted forms, elicited differential responses in the cell cycle of nontumorigenic and tumorigenic human cells in vitro. Although it is not yet understood why 20(S)-camptothecin and some of its substituted forms are cytostatic for nontumorigenic cells and cytotoxic for tumorigenic cells, the selective toxicity of the compounds against tumorigenic cells in vitro and in vivo was an especially interesting feature of these drugs.

Investigators began to experiment with various substituted forms of 20(S)-camptothecin. Good activity was found when various substitutions were made to the 20(S)-camptothecin scaffold. For example, 9-Amino-20(S)-Camptothecin (9AC) and 10,11-Methylendioxy-20(S)-Camptothecin (10,11 MD) are capable of having high anticancer activity against human colon cancer xenografts. Giovanella, B. C., et al., *Highly effective topoisomerase-I targeted chemotherapy of human colon cancer in xenogcrafts*, Science 246:1046–1048 (1989).

Additionally, 9-nitrocamptothecin (9NC) has shown high activity against human tumor xenograft models. 9NC has a nine position hydrogen substituted with a nitro moiety. 9NC has inhibited the growth of human tumor xenografts in immunodeficient nude mice and has induced regression of human tumors established as xenografts in nude mice with little or no appearance of any measurable toxicity. D. Chatterjee et al., *Induction of Apoptosis in Malignant and Camptothecin-resistant Human Cells*, 803 Annals of the New York Academy of Sciences 143 (1996).

U.S. Pat. No. 5,552,154 to Giovanella et al. disclosed methods of treating specific forms of cancer with water-insoluble 20(S)-camptothecin and derivatives thereof, having the closed-lactone ring intact. In particular, transdermal, oral and intramuscular methods of administration using solutions of water-insoluble 20(S)-camptothecin were disclosed.

Other substituted 20(S)-camptothecin compounds that have shown promise include 7-ethyl-10-hydroxy 20(S)-camptothecin, and other 7, 9, 10, 11-substituted compounds.

A continuing need exists to develop new and improved ways to exploit the useful therapeutic activities of 20(S)-camptothecin and its various derivatives and analogs.

SUMMARY OF THE INVENTION

The present invention provide new and improved compositions, kits, and methods for treating diseases using a combination therapy which includes 20(S)-camptothecin, an analog of 20(S)-camptothecin, a derivative of 20(S)-camptothecin, a prodrug of 20(S)-camptothecin, or a pharmaceutically active metabolite of 20(S)-camptothecin, collectively referred to herein as CPT. A therapeutic agent which exhibits a therapeutic synergistic effect with CPT is preferably employed in the therapy.

A wide variety of non-CPT therapeutic agents with therapeutic synergistic effects with CPT may be employed. Examples of the non-CPT therapeutic agent include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine.

Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel).

Examples of biologic agents include, but are not limited to, immuno-modulating proteins such as cytokines, monoclonal antibodies against tumor antigens, tumor suppressor genes, and cancer vaccines.

Examples of interleukins that may be used in conjunction with CPT include, but are not limited to, interleukin 2 (IL-2), and interleukin 4 (IL-4), interleukin 12 (IL-12). Examples of interferons that may be used in conjunction with CPT include, but are not limited to, interferon α, interferon β (fibroblast interferon) and interferon γ (fibroblast interferon). Examples of such cytokines include, but are not limited to erythropoietin (epoietin α), granulocyte-CSF (filgrastin), and granulocyte, macrophage-CSF (sargramostim). Other immunomodulating agents other than cytokines include, but are not limited to bacillus Calmette-Guerin, levamisole, and octreotide.

Example of monoclonal antibodies against tumor antigens that can be used in conjunction with CPT include, but are not limited to, HERCEPTIN® (Trastruzumab) and RITUXAN® (Rituximab).

Examples of the tumor suppressor genes include, but are not limited to, DPC-4, NF-1, NF-2, RB, p53, WT1, BRCA1 and BRCA2.

Example of cancer vaccines include, but are not limited to gangliosides (GM2), prostate specific antigen (PSA), α-fetoprotein (AFP), carcinoembryonic antigen (CEA) (produced by colon cancers and other adenocarcinomas, e.g. breast, lung, gastric, and pancreas cancers), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

The present invention also provides a method for treating undesired or uncontrolled angiogenesis. In one embodiment, the method comprises administering to a patient suffering from uncontrolled angiogenesis a therapeutically effective amount of CPT, such that formation of blood vessels is inhibited. In another embodiment, the method comprises administering to a patient suffering from uncontrolled angiogenesis a therapeutically effective amount of CPT and one or more non-CPT anti-angiogenesis agent, such that formation of blood vessels is inhibited. embodiment, Examples of non-CPT anti-angiogenesis agents include, but are not limited to, retinoid acid and derivatives thereof, 2-methoxyestradiol, ANGIOSTATIN™ protein, ENDOSTATIN™ protein,suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((l-azetidine-2-carboxylic acid (LACA), cishydroxyproline, d,l-3,4-dehydroproline, thiaproline], α, α-dipyridyl, beta.-aminopropionitrile fumarate, 4-propyl-5-(4-pyridinyl)2(3h)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), betay.-1-anticollagenase-Serum, alpha.2-antiplasmin, bisantrene, lobenzarit disodium, n-(2-carboxyphenyl-4-chloroanthronilic acid disodium or "CCA", thalidomide; angostatic steroid, cargboxynaminolmidazole; metalloproteinase inhibitors such as BB94. Other anti-angiogenesis agents include antibodies, such as monoclonal antibodies against these angiogenic growth factors: bFGF, aFGF, FGF-5, VEGF isoforms, VEGF-C, HGF/SF and Ang-1/Ang-2.

The method may be used to treat a wide variety of indications for which CPT has therapeutic activity. Such indications include, but are not limited to, restenosis (e.g. coronary, carotid, and cerebral lesions), benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Examples of benign tumors include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

Specific types of cancers include, but are not limited to, leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Diseases associated with abnormal angiogenesis include, but are not limited to, rheumatoid arthritis, ischemic-reperfusion related brain edema and injury, cortical ischemia, ovarian hyperplasia and hypervascularity, (polycystic ovary syndrom), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disese, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy.

Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

DETAILED DESCRIPTION OF THE INVENTION

1. CAMPTOTHECIN COMPOUNDS (CPT)

The class of camptothecin compounds referred to herein as CPT include various 20(S)-camptothecins, analogs of 20(S)camptothecin, derivatives of 20(S)-camptothecin, prodrugsof 20(S)camptothecin, and pharmaceutically active metabolites of 20(S)camptothecin. Camptothecin, when used in the context of this invention, includes the plant alkaloid 20(S)-camptothecin, both substituted and unsubstituted camptothecins, and analogs thereof. Examples of camptothecin derivatives include, but are not limited to, 9-nitro-20(S)-camptothecin, 9-amino-20(S)-camptothecin, 9-methylcamptothecin, 9-chloro-camptothecin, 9-flouro-camptothecin, 7-ethyl camptothecin, 10-methyl-camptothecin, 10-chloro--camptothecin, 10-bromo-camptothecin, 10-fluoro-camptothecin, 9-methoxycamptothecin, 11-fluoro-camptothecin, 7-ethyl-10-hydroxy camptothecin, 10,11-methylenedioxy camptothecin, and 10,11-ethylenedioxy camptothecin, and 7-(4-methylpiperazinomethylene) 10,11-methylenedioxy camptothecin. Prodrugs of camptothecin include, but are not limited to, esterified camptothecin derivatives as decribed in U.S. Pat. No. 5,731,316, such as camptothecin 20-O-propionate, camptothecin 20-O-butyrate, camptothecin 20-O-valerate, camptothecin 20-O-heptanoate, camptothecin 20-O-nonanoate, camptothecin 20-O-crotonate, camptothecin 20-O-2',3'-epoxy-butyrate, nitrocamptothecin 20-O-acetate, nitrocamptothecin 20-O-propionate, and nitrocamptothecin 20-O-butyrate.

In particular, when substituted camptothecins are used, a large range of substitutions may be made to the camptothecin scaffold, while still retaining activity. In a preferable embodiment, the camptothecin scaffold is substituted at the 7, 9, 10,11, and/or 12 positions. Such preferable substitutions may serve to provide differential activities over the unsubstituted camptothecin compound. Especially preferable are 9-nitrocamptothecin, 9-aminocamptothecin, 10,11-methylendioxy-20(S)-camptothecin, topotecan, irinotecan, 7-ethyl-10-hydroxy camptothecin, or another substituted camptothecin that is substituted at least one of the 7, 9, 10,11, or 12 positions.

Native, unsubstituted, camptothecin can be obtained by purification of the natural extract, or may be obtained from the Stehlin Foundation for Cancer Research (Houston, Tex.). Substituted camptothecins can be obtained using methods known in the literature, or can be obtained from commercial suppliers. For example, 9-nitrocamptothecin may be obtained from SuperGen, Inc. (San Ramon, Calif. and 9-aminocamptothecin may be obtained from Idec Pharmaceuticals (San Diego, Calif.). Camptothecin and various of its analogs may also be obtained from standard fine chemical supply houses, such as Sigma Chemicals.

Particular examples of 20(S)-camptothecins include 9-nitrocamptothecin, 9-aminocamptothecin, 10,11-methylendioxy-20(S)camptothecin, topotecan, irinotecan, 7-ethyl-10-hydroxy camptothecin, or another substituted camptothecin that is substituted at least one of the 7, 9, 10, 11, or 12 positions. These camptothecins may optionally be substituted.

2. NON-CPT THERAPEUTIC AGENTS

A wide variety non-CPT therapeutic agents may have a therapeutic additive or synergistic effect with CPT. Such non-CPT therapeutic agents may be hyperplastic inhibitory agents that addictively or synergistically combine with CPT to inhibit undesirable cell growth, such as inappropriate cell growth resulting in undesirable benign conditions or tumor growth. Examples of such non-CPT therapeutic agents include, but are not limited to, alkylating agents, antibiotic agents, antimetabolic agents, hormonal agents, plant-derived agents, and biologic agents.

The alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death.

Combination therapy including CPT and the alkylating agent may have therapeutic synergistic effects on cancer and reduce sides affects associated with these chemotherapeutic agents.

The antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interferes with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including CPT and the antibiotic agent may have therapeutic synergistic effects on cancer and reduce sides affects associated with these chemotherapeutic agents.

The antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including CPT and the antimetabolic agent may have therapeutic synergistic effects on cancer and reduce sides affects associated with these chemotherapeutic agents.

The hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including CPT and the hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Combination therapy including CPT and the plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immunomodulating proteins such as cytokines, monoclonal antibodies against tumor antigens, tumor suppressor genes, and cancer vaccines. Combination therapy including CPT and the biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon α (IFN-α) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with CPT include, but are not limited to, interleukin 2 (IL-2), and interleukin 4 (IL-4), interleukin 12 (IL-12).

Interferon α include more than 23 related subtypes with overlapping activities, all of the IFN-α subtypes within the scope of the present invention. IFN-α has demonstrated activity against many solid and hematologic malignancies, the later appearing to be particularly sensitive. Examples of interferons that may be used in conjunction with CPT include, but are not limited to, interferon α, interferon β (fibroblast interferon) and interferon γ (fibroblast interferon).

Other cytokines that may be used in conjunction with CPT include those cytokines that exert profound effects on hematopoiesis and immune functions. Examples of such cytokines include, but are not limited to erythropoietin (epoietin α), granulocyte-CSF (filgrastin), and granulocyte, macrophage-CSF (sargramostim). These cytokines may be used in conjunction with CPT to reduce chemotherapy-induced myelopoietic toxicity.

Other immuno-modulating agents other than cytokines may also be used in conjunction with CPT to inhibit abnormal cell growth. Examples of such immuno-modulating agents include, but are not limited to bacillus Calmette-Guerin, levamisole, and octreotide, a long-acting octapeptide that mimics the effects of the naturally occuring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including CPT and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant CD20⁺ pre-B and mature B cells. RITUXAN® is used as single agent for the treatment of patients with relapsed or refractory low-grade or follicular, CD20+, B cell non-Hodgkin's lymphoma. Combination therapy including CPT and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutions in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including CPT and tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TMs provide targets for the immune system to recognize and cause their destruction. Example of TMs include, but are not limited to gangliosides (GM2), prostate specific antigen (PSA), α-(fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/lysates of antologous tumor cells and allogeneic tumor cells.

An adjuvant may be used to augment the immune response to TMs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

A combination therapy including CPT and cancer vaccines may have therapeutic synergistic effects on tumors, which would potentially reduce the dosage of CPT needed for effective treatment. Thus, side effects associatec with non-specific cytotoxicity due to high doses of chemotherapeutic agent can be reduced.

3. INDICATIONS FOR TREATMENT WITH CPT

Preferable indications that may be treated using the combination therapies of the present invention include those involving undesirable or uncontrolled cell proliferation. Such indications include restenosis (e.g. coronary, carotid, and cerebral lesions), benign tumors, a various types of cancers such as primary tumors and tumor metastasis, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a melignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primerary and secondary. Primary tumors arise directly from the tissue in which they are found. A secondary tumor, or metastasis, is a tumor which originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrom), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanim of various angiogenic factors, including elements of the inflammatory response, such as leukocytes, platelets, cytokines, and eicosanoids, or unidentified plasma constituents have yet to be revealed.

In another embodiment of the present invention, a method is provided for treating diseases associated with undesired and uncontrolled angiogenesis. The method comprises administering to a patient suffering from uncontrolled angiogenesis a therapeutically effective amount of CPT, such that formation of blood vessels is inhibited. The particular dosage of CPT requires to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, CPT may be used to treat a variety of diseases associated with uncontrolled angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vritis, mycobacterial infections, Lyme's disese, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment of the present invention, a method is provided for treating chronic inflammatory diseases associated with uncontrolled angiogenesis. The method comprises administering CPT to a patient suffering from a chronic inflammatory disease associated with uncontrolled angiogenesis a therapeutically effective amount of CPT, such that formation of blood vessels is inhibited. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using CPT alone or in conjunction with other anti-inflammatory agents may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rhematoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by CPT should inhibit the formation of the sprouts and prevent the formation of granulomas. The inflammatory bowel diseases also exhibit extra intestinal manifectations, such as skin lesions. Such lesions are characterized by inflammation and angiogenesis and can occur at many sites other the gastrointestinal tract. Inhibition of angiogenesis by CPT should reduce the influx of inflammatory cells and prevent the lesion formation.

Sarcoidois, another chronic inflammatory disease, is characterized as a multisystem granulomatous disorder. The granulomas of this disease can form anywhere in the body and, thus, the symtoms depend on the site of the granulomas and whether the disease is active. The granulomas are created by the angiogenic capillary sprouts providing a constant supply of inflammatory cells. By using CPT to inhibit angionesis, such granulomas formation can be inhibited. Psoriasis, also a chronic and recurrent inflammatory disease, is characterized by papules and plaques of various sizes. Treatment using CPT alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using CPT alone or in conjunction with other anti-RA agents should prevent the formation of new blood vessels necessary to maintain the chronic inflammation and provide the RA patient relief from the symptoms.

CPT may also be used in conjunction with other antiangiogenesis agents to inhibit undesirable and uncontrolled angiogenesis. Examples of anti-angiogenesis agents include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-I, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((I-azetidine-2-carboxylic acid (LACA), cishydroxyproline, d,I-3,4-dehydroproline, thiaproline], α, α-dipyridyl, .beta.-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, beta.-cyclodextrin tetradecasulfate, eponemycin; fumagillin, gold sodium thiomalate, d-penicillamine (CDPT), beta.-1-anticollagenase-serum, alpha.2-antiplasmin, bisantrene, lobenzarit disodium, n-(2-carboxyphenyl-4-chloroanthronilic acid disodium or "CCA", thalidomide; angostatic steroid, cargboxynaminolmidazole; metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

4. COMPOSITIONS, FORMULATIONS, AND KITS

Compositions according to the present invention might include a CPT, a non-CPT therapeutic agent, together with a pharmaceutical excipient. The composition preferably have a therapeutic synergy in the treatment of a disease, or a synergistic effect on the subjected being treated. As used herein, a synergistic effect is achieved when a greater therapeutic effect results with a combination therapy than using either drug or monotherapy alone. One advantage of combination therapy with a synergistic effect is that lower dosages of one or both of the drugs or therapies may be used so that the therapeutic index is increased and toxic side effects are reduced.

In an aspect, the invention is directed to kits for treating diseases associated with abnormal cell proliferation. In one embodiment, the kit comprises a container that contains a compound selected from the group consisting of 20(S)-camptothecin, analog of 20(S)-camptothecin, derivative of 20(S)-camptothecin, prodrug of 20(S)-camptothecin, and pharmaceutically active metabolite of 20(S)-camptothecin; and one or more agents selected from the group conisting of alkylating agent, antibiotic agent, antimetabolic agent, hormonal agent, plant-derived agent, anti-angiogenesis agent and biologic agent.

According to this embodiment, the 20(S)-camptothecin may be 9-nitrocamptothecin, or 9-aminocamptothecin. Also according this embodiment, the biological agent may an immuno-modulating protein, monoclonal antibody against tumor antigen, tumor suppressor gene, or cancer vaccine. Other examples of the 20(S)-camptothecin, analogs of 20(S)-camptothecin, derivatives of 20(S)-camptothecin, prodrugs of 20(S)-camptothecin, and pharmaceutically active metabolites of 20(S)-camptothecin are listed in Section 1. Other examples of the alkylating agent, antibiotic agent, antimetabolic agent, hormonal agent, plantderived agent, anti-angiogenesis agent and biologic agent are listed in Section 2.

5. DELIVERY OF THERAPEUTIC AGENTS

A wide variety of delivery methods and formulations for different delivery methods are intended to be encompassed by the combination therapies of the present invention.

The inventive combination of therapeutic agents may be administered as compositions that comprise the inventive combination of therapeutic agents. Such compositions may include, in addition to the inventive combination of therapeutic agents, conventional pharmaceutical excipients, and other conventional, pharmaceutically inactive agents. Additionally, the compositions may include active agents in addition to the inventive combination of therapeutic agents. These additional active agents may include additional compounds according to the invention, or one or more other pharmaceutically active agents. In preferable embodiments, the inventive compositions will contain the active agents, including the inventive combination of therapeutic agents, in an amount effective to treat an indication of interest.

The inventive combination of therapeutic agents and/or compositions may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The inventive combination of therapeutic agents and compositions may be administered by a variety of routes, and may be administered or coadministered in any conventional dosage form. Coadministration in the context of this invention is defined to mean the administration of more than one therapeutic in the course of a coordinated treatment to achieve an improved clinical outcome. Such coadministration may also be coextensive, that is, occurring during overlapping periods of time.

One therapeutically interesting route of administration or coadministration is local delivery. Local delivery of inhibitory amounts of inventive combination of therapeutic agents and/or compositions can be by a variety of techniques and structures that administer the inventive combination of therapeutic agents and/or compositions at or near a desired site. Examples of local delivery techniques and structures are not intended to be limiting but rather as illustrative of the techniques and structures available. Examples include local delivery catheters, site specific carriers, implants, direct injection, or direct applications.

Local delivery by a catheter allows the administration of a inventive combination of therapeutic agents and/or compositions directly to the desired site. Examples of local delivery using a balloon catheter are described in EP 383 492 A2 and U.S. Pat. No. 4,636,195 to Wolinsky. Additional examples of local, catheter-based techniques and structures are disclosed in U.S. Pat. No. 5,049,132 to Shaffer et al. and U.S. Pat No. 5,286,254 to Shapland et al.

Generally, the catheter must be placed such that the inventive combination of therapeutic agents s and/or compositions can be delivered at or near the desired site. Dosages delivered through the catheter can vary, according to determinations made by one of skill, but often are in amounts effective to create a cytotoxic or cytostatic effect at the desired site. Preferably, these total amounts are less than the total amounts for systemic administration of the inventive combination of therapeutic agents and/or compositions, and are less than the maximum tolerated dose. The inventive combination of therapeutic agents s and/or compositions delivered through catheters preferably should be formulated to a viscosity that enables delivery through a small treatment catheter, and may be formulated with pharmaceutically acceptable additional ingredients (active and inactive).

Local delivery by an implant describes the placement of a matrix that contains the inventive combination of therapeutic agents s and/or compositions into the desired site. The implant may be deposited by surgery or other means. The implanted matrix releases the inventive combination of therapeutic agents s and/or compositions by diffusion, chemical reaction, solvent activators, or other equivalent mechanisms. Examples are set forth in Lange, *Science* 249:1527–1533 (September, 1990). Often the implants may be in a form that releases the inventive combination of therapeutic agents s and/or compositions over time; these implants are termed time-release implants. The material of construction for the implants will vary according to the nature of the implant and the specific use to which it will be put. For example, biostable implants may have a rigid or semi-rigid support structure, with inventive combination of therapeutic agents and/or composition delivery taking place through a coating or a porous support structure. Other implants made be made of a liquid that stiffens after being implanted or may be made of a gel. The amounts of inventive combination of therapeutic agents and/or composition present in or on the implant may be in an amount effective to treat cell proliferation generally, or a specific proliferation indication, such as the indications discussed herein.

One example of local delivery of the inventive combination of therapeutic agents and/or composition by an implant is use of a biostable or bioabsorbable plug or patch or similar geometry that can deliver the inventive combination of therapeutic agents and/or composition once placed in or near the desired site. An example of such implants can be found in U.S. Pat. No. 5,429,634 to Narciso, Jr.

A particular application of use of an implant according to the invention is treatment of cell proliferation in tissue that is not highly vascularized, as discussed briefly above. An example of such tissue is bone tissue. The difficulty in treating uncontrolled proliferative cell growth in bone tissue may be exemplified by the difficulties in treating bone tumors. Such tumors are typically refractory to treatment, in part because bone tissue is not highly vascularized. An implant in or near the proliferative site may potentially have localized cytotoxic or cytostatic effects with regard to the proliferative site. Therefore, in one embodiment, the invention may be used to treat bone tumors.

Another example of local delivery by an implant is the use of a stent. Stents are designed to mechanically prevent the collapse and reocclusion of the coronary arteries. Incorporating an inventive combination of therapeutic agents and/or composition into the stent may deliver the agent directly to or near the proliferative site. Certain aspects of local delivery by such techniques and structures are described in Kohn, *Pharmaceutical Technology* (October, 1990). Stents may be coated with the inventive combination of therapeutic agents and/or composition to be delivered. Examples of such techniques and structures may be found in U.S. Pat. No. 5,464,650 to Berg et al., U.S. Pat. No. 5,545,208 to Wolff et al., U.S. Pat. No. 5,649,977 to Campbell, U.S. Pat. No. 5,679,400 to Tuch, EP 0 716 836 to Tartaglia et al. Alternatively, the inventive combination of therapeutic agents and/or composition loaded stent may be biorotable, i.e. designed to dissolve, thus releasing the inventive combination of therapeutic agents and/or composition in or near the desired site, as disclosed in U.S. Pat. No. 5,527,337 to Stack et al. The present invention can be used with a wide variety of stent configurations, including, but not limited to shape memory alloy stents, expandable stents, and stents formed in situ.

Amounts of the inventive combination of therapeutic agents and/or composition delivered by the stent can vary, according to determinations made by one of skill, but preferably are in amounts effective to create a cytotoxic or cytostatic effect at the desired site. Preferably, these total amounts are less than the total amounts for systemic administration of the inventive combination of therapeutic agents and/or composition, and are preferably less than the maximum tolerated dose. Appropriate release times can vary, but preferably should last from about 1 hour to about 6 months, most preferably from about 1 week to about 4 weeks. Formulations including the inventive combination of therapeutic agents and/or composition for delivery of the agent via the stent can vary, as determinable by one of skill, according to the particular situation, and as generally taught herein.

Another example is a delivery system in which a polymer that contains the inventive combination of therapeutic agents and/or composition is injected into the target cells in liquid form. The polymer then cures to form the implant in situ. One variation of this technique and structure is described in WO 90/03768 to Donn.

Another example is the delivery of the inventive combination of therapeutic agents and/or composition by polymeric endoluminal sealing. This technique and structure uses a catheter to apply a polymeric implant to the interior surface of the lumen. The inventive combination of therapeutic agents and/or composition incorporated into the biodegradable polymer implant is thereby released at the desired site. One example of this technique and structure is described in WO 90/01969 to Schindler.

Another example of local delivery by an implant is by direct injection of vesicles or microparticulates into the desired site. These microparticulates may comprise substances such as proteins, lipids, carbohydrates or synthetic polymers. These microparticulates have the inventive combination of therapeutic agents and/or composition incorporated throughout the microparticle or over the microparticle as a coating. Examples of delivery systems incorporating microparticulates are described in Lange, *Science*, 249:1527–1533 (September, 1990) and Mathiowitz, et al., *J. App. Poly Sci.* 26:809 (1981).

Local delivery by site specific carriers describes attaching the inventive combination of therapeutic agents and/or composition to a carrier which will direct the drug to the desired site. Examples of this delivery technique and structure include the use of carriers such as a protein ligand or a monoclonal antibody. Certain aspects of these techniques and structures are described in Lange, *Science* 249:1527–1533.

Local delivery also includes the use of topical applications. An example of a local delivery by topical application is applying the inventive combination of therapeutic agents and/or composition directly to an arterial bypass graft during a surgical procedure. Other equivalent examples will no doubt occur to one of skill in the art.

The inventive combination of therapeutic agents s and/or compositions may be used in the form of kits. The arrangement and construction of such kits is conventionally known to one of skill in the art. Such kits may include containers for containing the inventive combination of therapeutic agents s and/or compositions, and/or other apparatus for administering the inventive combination of therapeutic agents and/or compositions.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

what is claimed is:

1. A method for treating cancer with a combination therapy, comprising:

administering to a patient suffering from cancer that is sensitive to the combination therapy a therapeutically effective amount of 9-nitro-20(S)-camptothecin, in combination with a therapeutically effective amount of an antibody against the cancer cells, such that the efficacy of the therapy is enhanced through synergistic effects of 9-nitro-20(S)-camptothecin and the antibody, wherein the antibody is selected from the group consisting of Trastruzumab, or Ritrastrumab.

2. The method according to claim 1, wherein the cancer is selected from the group consisting of leukemia, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas.

3. A kit for treating cancer with a combination therapy, comprising:

a container that contains a therapeutically effective amount of 9-nitro-20(S)-camptothecin, and a therapeutically effective amount of an antibody against the cancer cells wherein the antibody is selected from the group consisting of Trastruzumab or Riturimab wherein the therapy is enhanced through synergistic effects of 9-nitro-20(S)-camptothecin and the antibody.

* * * * *